US010613076B2

(12) United States Patent
Meller et al.

(10) Patent No.: US 10,613,076 B2
(45) Date of Patent: Apr. 7, 2020

(54) OPTOELECTRONIC CONTROL OF SOLID-STATE NANOPORES (71) Applicant: The Trustees of Boston University, Boston, MA (US)

(72) Inventors: Amit Meller, Brookline, MA (US); Nicolas Di Fiori, Brookline, MA (US)

(73) Assignee: THE TRUSTEES OF BOSTON UNIVERSITY, Boston, MA (US)

(*) Notice: Subject to any disclaimer, the term of this patent is extended or adjusted under 35 U.S.C. 154(b) by 688 days.

(21) Appl. No.: 14/775,217

(22) PCT Filed: Mar. 14, 2014

(86) PCT No.: PCT/US2014/028825
§ 371 (c)(1),
(2) Date: Sep. 11, 2015

(87) PCT Pub. No.: WO2014/153047
PCT Pub. Date: Sep. 25, 2014

(65) Prior Publication Data
US 2016/0033471 A1 Feb. 4, 2016

Related U.S. Application Data (60) Provisional application No. 61/783,606, filed on Mar. 14, 2013.

(51) Int. Cl.
*G01N 33/00* (2006.01)
*G01N 33/487* (2006.01)
(Continued)

(52) U.S. Cl.
CPC ..... *G01N 33/48721* (2013.01); *C12Q 1/6869* (2013.01); *G01N 21/63* (2013.01); *G01N 27/49* (2013.01); *G01N 2201/06113* (2013.01)

(58) Field of Classification Search
None
See application file for complete search history.

(56) References Cited

U.S. PATENT DOCUMENTS 6,042,994 A * 3/2000 Yang ............... B05D 3/068
257/E21.271
2005/0127035 A1 * 6/2005 Ling ................ B82Y 5/00
216/56

(Continued)

OTHER PUBLICATIONS

Instructions for the JEM-2010F Field-Emission Transmission Electron Microscope, published Aug. 2011; [retrieved on Jan. 16, 2018]. Retrieved from the Internet: <URL: www.mri.psu.edu/sites/default/files/file_attach/JEM-2010F_SOP.pdf. (Year: 2011).*

(Continued)

*Primary Examiner* — Robert T. Crow
(74) *Attorney, Agent, or Firm* — Wilmer Cutler Pickering; Hale and Dorr LLP (57) ABSTRACT

Optoelectronic control of solid-state nanopores and applications thereof. Nanopores are extremely sensitive single-molecule sensors. Electron beams have been used to fabricate synthetic nanopores in thin solid-state membranes with sub-nanometer resolution. Methods for controlling the translocation speed of biopolymers through solid-state nanopores and methods for unblocking clogged pores by illuminating nanopores are described.

12 Claims, 6 Drawing Sheets

(51) Int. Cl.
*C12Q 1/6869* (2018.01)
*G01N 21/63* (2006.01)
*G01N 27/49* (2006.01)

(56) References Cited

U.S. PATENT DOCUMENTS

| | | | |
|---|---|---|---|
| 2005/0161589 A1* | 7/2005 | Kim | B82Y 20/00 |
| | | | 250/216 |
| 2005/0241933 A1* | 11/2005 | Branton | B82Y 15/00 |
| | | | 204/192.34 |
| 2005/0255581 A1 | 11/2005 | Kim et al. | |
| 2006/0003458 A1* | 1/2006 | Golovchenko | C12Q 1/6811 |
| | | | 436/86 |
| 2010/0289505 A1* | 11/2010 | Zhang | C12Q 1/6869 |
| | | | 324/663 |
| 2011/0053284 A1 | 3/2011 | Meller et al. | |
| 2011/0117582 A1* | 5/2011 | Malima | G01N 33/5438 |
| | | | 435/7.92 |
| 2011/0308950 A1 | 12/2011 | Sakai et al. | |
| 2013/0176563 A1 | 7/2013 | Ozawa et al. | |

OTHER PUBLICATIONS

Prashanth et al, J. Asian. Ceramic Soc., vol. 3, pp. 345/351 (2015). (Year: 2015).*
Abgrall et al, Anal. Chem., vol. 80, pp. 2326-2341, published online Mar. 6, 2008.*
Kasianowicz et al., "Characterization of individual polynucleotide molecules using a membrane channel," Proc. Nat. Acad. Sci. 93, pp. 13770-13773 (1996).
Akeson et al., "Microsecond time-scale discrimination among polycytidylic acid, polyadenylic acid, and polyuridylic acid as homopolymers or as segments within single RNA molecules," Biophys. J. 77, 3227-3233 (1999).
Meller et al., "Rapid nanopore discrimination between single polynucleotide molecules," Proc Nat Acad Sci 97:3, pp. 1079-1084 (2000).
Bezrukov et al., "Counting polymers moving through a single ion channel," Nature 370, 279-281 (1994).
Dekker, "Solid-state nanopores," Nature Nanotechnology, 2, pp. 209-215 (2007).
Di Fiori et al., "Optoelectronic control of surface charge and translocation dynamics in solid-state nanopores," Nature Nanotechnology 8(12), pp. 946-951 (2013).
International Search Report and Written Opinion for International Patent Application No. PCT/US14/28825 dated Aug. 5, 2014 (14 pages).
Ke, "Applications of Tightly Focused Ultrafast Laser in the Fabrication of Micro Total Analysis Systems and Biological Research," Doctoral Dissertation, The University of Michigan, pp. 1-123 (2008).
Smeets et al., "Nanobubbles in Solid-State Nanopores," Physical Review Letters 97, pp. 088101-1-088101-4 (2006).
Trepagnier et al., "Controlling DNA Capture and Propagation through Artificial Nanopores," Nano Letters, 7(9), pp. 2824-2830 (2007).
Venkatesan et al, "DNA Sensing Using Nanocrystalline Surface-Enhanced $Al_2O_3$ Nanopore Sensors," Advanced Functional Materials 10(8), pp. 1266-1275 (2010).

* cited by examiner

OPTOELECTRONIC CONTROL OF SOLID-STATE NANOPORES

CROSS REFERENCE TO RELATED APPLICATION

This application is a national stage application of International Application No. PCT/US14/028825, filed on Mar. 14, 2014 and claims the benefit of U.S. Provisional Application No. 61/783,606, filed Mar. 14, 2013, the contents of which are hereby incorporated by reference.

GOVERNMENT SUPPORT

This invention was made with Government Support under Contract No. HG-005871 awarded by the National Institute of Health and Contract No. PHY0646637 awarded by the National Science Foundation. The Government has certain rights in the invention.

BACKGROUND

1. Technical Field

The present invention relates to optoelectronic control of solid-state nanopores and nanopore arrays, and applications thereof.

2. Discussion of Related Art

Nanopores, pores of nanometer dimensions in an electrically insulating membrane, have shown promise for use in a variety of sensing applications, including single molecule detectors. The nanopores used in such applications can be biological protein channels in a lipid bilayer or a pore in a solid-state membrane. Solid-state nanopores are generally made in silicon compound membranes, one of the most common being silicon nitride. Solid-state nanopores can be manufactured with several techniques including ion-beam sculpting of silicon nitride and using e-beam lithography.

The use of nanopores in single-molecule detection employs a detection principle based on monitoring the ionic current of an electrolyte solution passing through the nanopore as a voltage is applied across the membrane. When the nanopore is of molecular dimensions, passage of molecules causes interruptions in the open pore current level. The temporal variation in current levels leads to a translocation event pulse. These detection methods are described at length in: Kasianowicz JJ, Brandin E, Branton D, Deamer D W, (1996) "Characterization of individual polynucleotide molecules using a membrane channel." Proc Nat Acad Sci 93:13770-13773; Akeson, M, Branton, D, Kasianowicz J, Brandin E, and Deamer D, (1999) Biophys. J. 77: 3227-3233; Meller A, Nivon L, Brandin E, Golovchenko J, Branton D, (2000) Proc Nat Acad Sci 97: 1079-1084, all of which are herein incorporated by reference in their entireties.

Nanopore detection techniques have been used for biomolecule detection. For example, various nanopore sequencing methods have been proposed. In 1994, Bezrukov, Vodyanoy and Parsegian showed that one can use a biological nanopore as a Coulter counter to count individual molecules (*Counting polymers moving through a single ion channel*, Nature 370, 279-281 (1994) incorporated herein by reference). In 1996, Kasianowicz, Brandin, Branton and Deamer proposed an ambitious idea for ultrafast single-molecule sequencing of single-stranded DNA molecules using nanopore ionic conductance as a sensing mechanism (*Characterization of individual polynucleotide molecules using a membrane channel*, Proc. Nat. Acad. Sci. USA 93 13770-13773 (1996), incorporated herein by reference).

The methods seek to effectively determine the order in which nucleotides occur on a DNA (or RNA) strand. The theory behind nanopore sequencing concerns observed behavior when the nanopore is immersed in a conducting fluid and a potential (voltage) is applied across it. Under these conditions an electrical current that results from the conduction of ions through the nanopore can be observed. The amount of current which flows is sensitive to the size of the nanopore. When a biomolecule passes through the nanopore, it will typically create a change in the magnitude of the current flowing through the nanopore. Electronic sensing techniques are used to detect the ion current variations, thereby sensing the presence of the biomolecules.

U.S. Pat. No. 6,428,959, the entire contents of which are herein incorporated by reference, describes methods for determining the presence of double-stranded nucleic acids in a sample. In the methods described, nucleic acids present in a fluid sample are translocated through a nanopore, e.g., by application of an electric field to the fluid sample. The current amplitude through the nanopore is monitored during the translocation process and changes in the amplitude are related to the passage of single- or double-stranded molecules through the nanopore. Those methods find use in a variety of applications in which the detection of the presence of double-stranded nucleic acids in a sample is desired.

There are numerous challenges to develop effective nanopore detection techniques. Two of the most significant challenges facing nanopore-assisted genomic sequencing are that molecular passage across the nanopore is higher than desired, and current throughput is lower than desired due to nanopores consistently getting permanently blocked. It would be desirable to provide solid-state nanopores with surface characteristics that can be selectively modified to modulate translocation speed and unblock clogged pores.

SUMMARY

The present application relates to optoelectronic control of solid-state nanopores and nanopore arrays, methods of forming nanopores and applications thereof.

In accordance with certain embodiments, light is used to induce and modulate surface charges at the nanometer scale in solid-state nanopores. The induced charges can be used to slow down the passage of nucleic acid molecules through the pore (i.e., translocation) in a switchable, reversible, non-intrusive, tunable and in-situ manner. Moreover, this process can be implemented using low-cost components. The ability to slow down translocations is advantageous in the field of nanopore-based sequencing due to the limits in bandwidth imposed by current technology. As described herein, the amount of slowing-down is proportional to the light intensity and can, in principle, slow down the passage enough to immobilize a single biopolymer inside the nanopore. Additionally, induced surface charges are able to immediately and repeatedly unblock clogged pores, rendering this technology essential in maintaining a healthy population of open, functioning pores. These discoveries address the two biggest challenges facing nanopore-assisted genomic sequencing: molecular passage across the nanopore is currently higher than desired, and current throughput is lower than desired due to nanopores consistently getting permanently blocked.

According to one embodiment of the invention, a method for characterizing an analyte is provided. The method includes providing a solid-state membrane comprising a nanopore submerged in a saline solution, optoelectronically modifying the surface of the nanopore to induce a measurable change in the nanopore ionic conductance not induced by a thermal effect, receiving the analyte through the nanopore, and detecting variations in current and/or variations in light emission from the analyte, wherein the variations in current and/or light emission correspond to interactions between the analyte and nanopore surface.

Under another aspect of the invention, the solid state insulating membrane includes a silicon nitride material.

Under another aspect of the invention, the nanopore surface may also include a chemical coating.

According to another embodiment of the invention, a method for inducing a charge on the surface of an aperture in a solid state membrane is provided. The method includes illuminating the surface of the aperture in a solid-state membrane with sufficient radiant energy from a light source to produce a measurable change in conductance of the pore not induced by a thermal effect. In accordance with some aspects, the change in conductance is an increase in conductance of at least 2%, 5%, 10%, 50%, 100, 150%, or 200%.

Under another aspect of the invention, the aperture includes an aperture having a diameter less than or equal to approximately 1-100 nanometers.

According to another embodiment of the invention, a method is provided that includes contacting a liquid containing a biopolymer with a solid-state insulating membrane having disposed therein a nanopore with at least one surface; causing the biopolymer to traverse the nanopore; and illuminating the surface of the nanopore with radiant energy from a light source to control the speed at which the biopolymer traverses the nanopore.

Under another aspect of the invention, the biopolymer includes one of single-stranded DNA, double-stranded DNA, RNA, and a polypeptide.

In accordance with another embodiment, a system for characterizing an analyte is provided. The system may include a solid-state membrane comprising a nanopore and a light source capable of optoelectronically modifying a surface of the nanopore to induce a charge on the nanopore surface. The system may also include a device for detecting the analyte. In accordance with one aspect, detection of the analyte involves detection of variations in current and/or light emission from the analyte during translocation of the analyte, wherein the variations in current correspond to interactions between the analyte and nanopore surface. In accordance with another aspect, detection of the analyte involves detection of variations in emitted light.

In accordance with another aspect, a method for characterizing an analyte using a nanopore array is provided. The method may involve selectively illuminating selected nanopores in the array with sufficient radiant energy from a light source to produce an increase in conductance of the selected nanopores of at least 2% to individually control the translocation speed of the analyte through each of the selected nanopores. Light can be directed to one location as opposed to other areas to control translocation speed in a particular nanopore. Each of the nanopores can be subject to independent exposure and control.

BRIEF DESCRIPTION OF THE DRAWINGS

FIG. 2A shows representative translocation events with and without illumination, showing the increase in $I_O$, $I_B$ and $t_D$.

FIG. 2B provides time traces showing the open pore current $I_O$, the blocked current amplitude $\Delta I$ (top panel), and the mean translocation time $<t_D>$ (lower panel). The net effect of the laser illumination is to increase $I_O$ and $t_D$ while keeping $\Delta I$ constant. All data points in $<t_D>$ represent a running average over 150 translocation events, initialized at the moment the laser is switched on/off. The Retardation Factor, RF, defined as the mean $t_D$ with light divided by the mean $t_D$ in darkness. In this example a factor of ~10 is obtained with P=2 mW.

FIG. 2C shows detection of the small molecular weight protein ubiquitin in its native state using a 5 nm nanopore, enabled by illumination of the chip with laser light. Typical translocation time traces are shown at P=0 and P=4 mW. With P=4 mW at least two orders of magnitude increase in the events' dwell times is observed. A typical translocation time distribution and fractional blockade current ($I_B$) of the ubiquitin under 4 mW of focused light are shown at the bottom (N>500). Under these conditions, two prominent timescales for ubiquitin translocation (340±5 $\mu s$ and 890±70 $\mu s$), as well as two peaks in the blockade currents (0.88 and 0.78), can be approximated by a sum of two Gaussians. The inset is an illustration of the crystallographic structure of wild type human ubiquitin (PDB 1d3z).

FIG. 3A provides plots of the ionic current enhancement I(P)/I(0) as a function of laser power for a 5, 10, 15, and 20 nm-diameter pores, as indicated.

FIG. 3B is a graph showing pore response to light, $\delta I/\delta P$, as obtained from linear fits to plots of I(P), as a function of pore diameter. The dependences on the current enhancement shown in FIG. 3A and of the pore response to light shown in FIG. 3B on pore size suggest that the origin of the photo-conductance effect resides on the pore's surface (i.e., pore walls) and not on its volumetric content.

FIG. 4A provides illustrations showing the bulk and surface ionic current terms discussed in the text, and the origin of the electro osmotic force acting to retard the DNA translocation for the same nanopore in darkness (left) and under laser illumination (right). Here $I_{surface}=I_{DL}+I_{EOF}$ (Eq.1)

FIG. 4B (left) is a graph showing the Retardation Factor (RF) as a function of laser intensity measured for different nanopore sizes: 4.3, 5.4, 5.6, 6.1, and 7.4 nm (diamonds, squares, upward triangles, circles and downward triangles, respectively) and DNA lengths: 400 bp (squares), 3.5 kbp (downward triangles), 5 kbp (upright triangles and diamonds), and 10 kbp (circles). Each data point was calculated from at least 1,000 events per laser intensity. FIG. 4B (right) is a graph showing RF as a function of the nanopore surface charge density calculated using the open pore current versus laser intensity for each pore (see Eq. 2 below). Remarkably, all data points collapse onto a single curve, regardless of DNA length or nanopore diameter.

FIG. 5A shows the laser intensity response time upon a TTL trigger measured by a fast photodiode, showing a rise time of <0.2 µs. FIG. 5B shows the simultaneous measurement of the pore current and laser intensity upon switching on the laser with the TTL pulse. The bottom panel displays the intensity of the laser pulse as a function of time (going from 0 to 5 mW at t=25 ms). The simultaneous measurement of the ionic current flowing through a 5 nm pore (V=300 mV, C=1 M KCl), shows an abrupt jump of the current from 4.4 nA to 7.1 nA. The delay time from switching on the laser light to the stabilization at the current at the higher level was measured to be 0.45 ms. The ion current response is subject to a transient saturation of the Axon amplifier.

DETAILED DESCRIPTION

Introduction

The present invention features devices and systems embodying one or more solid-state nanopores that can be used in a variety of sensing and detection applications. The modification of nanopores in thin, solid-state membranes through exposure to light enables these applications to function more efficiently than conventional systems. These applications include the characterization of single molecules, sequencing of DNA or RNA, pH sensing in an environment and, in certain cases, chemical transport. Nanoscale control over the surface properties of nanopores can govern the nanopore's interactions with various substances and environments. The present application details optoelectronic modification of solid-state nanopores and applications of modified nanopores.

Techniques for the optoelectronic control of nanopores, described below, have significant implications for the usefulness of thin, solid-state membranes in sensing and detection applications. These techniques enable the integration of nanopore sensing apparatus in a variety of systems. In this specification, thin, solid-state membranes should at least be understood to mean a thin layer of material having a thickness ranging between approximately 5 nanometers and approximately 100 nanometers and comprising an insulating (or semiconducting) inorganic compound, for example a Si-based material such as silicon oxide, silicon nitride, a mixture thereof, or various materials having energy bands accessible for excitation optically by UV, Visible or NIR light. Solid-state should be understood to encompass that group of materials typically defined as solid-state by the semiconductor industry with regard to various electronics applications. Nanopores should be understood to entail apertures of nanoscale dimensions formed in a membrane. In this specification, the aperture refers to a passage in a particular membrane, open to two opposite sides of the membrane. The surface of the aperture should be understood to mean at least the exposed surface of the membrane forming axially-oriented walls of the aperture. As used herein, nanometer-scale indicates linear dimensions between 0 and approximately 1,000 nanometers (nm). In this specification, interactions outside the nanopore will be referred to as "DNA/membrane interactions" to distinguish them from "DNA/Nanopore interactions" inside the nanopore, although the chemical nature of the two forms of interactions may be similar.

The present application relates to methods for optoelectronically modifying solid-state nanopore surfaces. Optoelectronically modifying a surface on the nanopore refers to light-induced charging of the nanopore surface(s) thus inducing a change in conductance of the nanopore using electromagnetic radiation. The electromagnetic radiation that may be used includes UV, visible, and NIR. Nanopores are small holes (approximately 1-100 nm diameter) in a partition ("membrane") whose thickness is of similar order. The membrane divides a volume into two separate compartments, each of which may contain different types and/or concentrations of analytes. In some embodiments, one or more pore(s) can provide a passage, and in some instances be the only passage, between these two compartments. When a voltage is applied across the membrane, an electric field develops across the nanopore. The applied electric field acts as a force on charged molecules and ions inside the nanopore. In the case of nanopore-immobilized molecules (e.g., enzymes), this electric field may also induce structural changes, which may in turn modulate their activity. Therefore, immobilization of proteins, enzymes or other forms of chemical functionalization at the nanopore juncture provides possibilities which have not been achieved by the immobilization of molecules on planar surfaces. Several applications, which are based on this property, are envisioned and described in detail below.

Nanopores have emerged in recent years as versatile single-molecule detectors. The sensing principle is based on transient interruptions in the ion-current of an electrolyte, induced by the entry, transport, and exit of a particular analyte from the pore. A distinguishing feature of nanopores is that they can be used to analyze not only small molecules, but also long biopolymers, such as DNA and RNA, with resolution on the order of the nanopore length (several nm). A well-studied system involves the lipid-embedded α-hemolysin (α-HL) protein pore, which can accommodate various types of biopolymers. α-HL has been used extensively to discriminate between DNA and RNA sequences, to study DNA unzipping kinetics, orientation of entry, DNA-protein interactions, and peptide transport. An important outcome of these studies has been the realization that threaded biopolymer dynamics is governed by the biopolymer's interactions with the nanopore walls. This notion has been utilized for the detection of small molecules, metal-ions, and the discrimination of enantiomer drugs, by employing molecular biology methods to modify the α-HL nanopore. However, the range of sensing applications using α-HL is limited by its fixed dimensions and the delicate nature of a lipid membrane.

To expand the realm of nanopore sensing, synthetic nanopores have been introduced using a variety of materials, such as polymers, glass, and thin solid-state membranes.

(See: PCT Patent Publ. No. WO2004/078640A1, Methods and apparatus for controlled manufacturing of nanometer-scale apertures, filed Mar. 5, 2003 by Storm et al., which is herein incorporated by reference in its entirety.) Such nanopores have demonstrated utility for sensing single-stranded and double-stranded DNA, ions, macromolecules, and proteins. (See, for example, Fologea, Gershow, Ledden, McNabb, Golovchenko and Li, *Detecting single stranded DNA with a solid state nanopore*, NanoLetters Vol. 5, No. 10 1905-1909 (2005), herein incorporated by reference in its entirety.) Nanopores incorporated in thin (~10 nm) solid-state inorganic membranes are highly promising materials, since the nanopore volume can be reduced to a few nm in all dimensions, on par with biological membrane channels. In addition, the planar geometry permits high-resolution fabrication and characterization using the transmission electron microscope (TEM), as exemplified by sub-nm size control for nanopores down to 1 nm diameters. Further, the fabrication of high-density nanopore arrays is possible, setting the stage for high-throughput biomolecular analysis, in particular ultra-fast DNA sequencing.

Various detection methods may be used and optical detection mechanisms may be preferable for certain embodiments. The present technology is highly scalable, with both optically- and electrically-addressable nanopore array assemblies enabling detection over a surface area.

Electrical detection mechanisms rely on ion current sensing as can be measured with an ammeter or electometer. Ion current sensing for individual nanopores and nanopore arrays typically uses a potassium chloride or other electrolyte solution (salt solution). A nanopore membrane separates two reservoirs of ionic solution. When voltage is applied across the two reservoirs, the potential drop almost entirely occurs at the nanopore. Therefore, the ionic conductance or resistance between the two reservoirs is also the conductance or resistance of the nanopore. The nanopore conductance transiently drops when a molecule (e.g., DNA) enters and exits the nanopore, allowing its detection. By analyzing the transient conductance spikes, the properties of biopolymers (size, charge, structure) can be investigated. This detection scheme can be parallelized using an array of nanopores with individual electrodes situated at each chamber. The individual electrodes are then uniquely addressable using techniques well-known in the semiconductor industry.

In one aspect, light can be directed to certain individual nanopores or a selected group of nanopores to control translocation speed at specific pores. Light intensity can also be varied on a pore by pore basis, for example by steering the optical beam by fast scanning mirrors, and directing the beam to each of the pores on a time shared basis. Light exposure conditions can be independently determined for each individual pore in the nanopore array.

The detection system may involve detection of variations in light emission from the analyte, wherein the variations in the emitted light correspond to interactions between the analyte and nanopore surface. The detection system in accordance with this aspect must be capable of detecting changes in optical properties of an optical agent on the time scale relevant to the method described herein. In one aspect, fluorophores are employed as optical agents. A suitable fluorescence detector therefore would be appropriate. Those skilled in the art are familiar with fluorescence detectors. Additional information regarding an optical detection system can be found in U.S. Pat. No. 7,972,858, the contents of which are hereby incorporated by reference.

In accordance with certain aspects of the present invention, the step of detecting variations in the ion current and/or light emission from the analyte may be determined by measuring the ionic conductance or resistance between the two reservoirs, which is also the conductance or resistance of the nanopore. The nanopore conductance transiently drops when a molecule (e.g., DNA) enters and exits the nanopore, allowing its detection. By analyzing the transient conductance spikes, the properties of biopolymers (size, charge, structure) can be investigated.

Analytes that can be detected using the methods described herein are not particularly limited. Non-limiting examples include nucleic acids, peptides, antigens, antibodies, and proteins. Analytes also include polymers such as copolymers, block copolymers, and branched polymers such as star polymers and dendrimers. Analytes may comprise nanoparticles. A mixture of analytes may be employed in embodiments herein. Analytes can be either charged or uncharged. Charged analytes are driven towards and through the nanopore under the influence of an electrical field; uncharged analytes diffuse and enter the pore stochastically.

Methods of Illuminating Solid-State Nanopores

Nanopores are extremely sensitive single-molecule sensors. Recently, electron beams have been used to fabricate synthetic nanopores in thin solid-state membranes with sub-nanometer resolution. This process holds the promise of becoming the next generation sequencing platform, achieving ultra-fast and low-cost DNA sequencing. Two attractive features of nanopores make it exceptionally useful for single molecule-based genome analysis: first, the ability to electrophoretically focus and thread extremely long DNA molecules from the bulk into the pore, making it possible to analyze minute DNA samples. Second, sub-5 nm pores are now routinely used to linearize long DNA coils, allowing nanopores to effectively "scan" information along a long genome. These features, together with the fact that solid-state nanopores can be fabricated in highly dense arrays, allow the development of massively parallel detection and are crucial for the realization of an amplification-free, low-cost, and high-throughput sequencing method.

In accordance with one aspect, a low-power focused laser beam of visible light interacts with the surface of the pore of a solid state membrane to induce reversible surface charges that scale linearly with the light intensity. When an external electric field is applied, these charges, in turn, create a net water flow (i.e., electro-osmotic flow). If the induced charges are negative, then the electro-osmotic flow will be directed in the direction opposite to the movement of the nucleic acid (which are positively charged). By modulating these charges with light it is possible to attune the electro-osmotic forces acting on the DNA (or any other biopolymer) as it is threaded through the charged nanopore, thus modulating the translocation speed. Over a 10-fold decrease in the translocation speed of a nucleic acid biopolymer in a nanopore having a dimension of 5-20 nm has been obtained using 1-10 mW of light. With a small protein, over a 100-fold decrease in translocation speed has been obtained using the method described herein. Reductions in speed that may be obtained may range from incremental reductions to reductions of greater than 100-fold, more particularly reduction by a factor of 2 to 25, more particularly 5-20, and in certain cases, of about 8-15 as compared to a nanopore system in which the pores are not illuminated as described herein. Even greater reductions in speed, up to and including complete immobilization of the analyte, may be realized.

In accordance with certain embodiments, the surface of the pore is illuminated with radiation from a light source. The radiation applied may comprise one or more wavelengths from the electromagnetic spectrum. Typically, the radiation comprises visible light (about 380 nm to about 750 nm). In accordance with certain aspects, other sources of radiation, such as ultraviolet and near infrared light may also be used. The light source may be a laser. Examples of suitable lasers include UV, VIS, and IR lasers such as nitrogen lasers, $CO_2$ lasers, Er-YAG lasers, Nd-YAG, Er-YTLF, Er-YSGG and the like. Typical laser powers which are useful are 1-1,000 milliwatts. Typical laser wavelengths are 200-750 nm (UV-VIS wavelengths). Particularly useful light sources include visible light lasers, such as a 532 nm laser or a 640 nm laser. Multiple forms of radiation may also be applied simultaneously, in combination or coordinated in a step-wise fashion. Radiation exposure may be constant over a period of time corresponding to the operation of the nanopore system, or varied with pulses at predetermined intervals.

The process of drilling nanopores in silicon nitride with an electron beam reduces the N/Si ratio due to the preferential ablation of N atoms, leaving behind Si-rich regions around the pores. Moreover, the principal defects in silicon-rich CVD amorphous SiNx materials are Si dangling bonds which can trap electrons or holes to become electrically charged, and when the N/Si ratio approaches 0.8 the band gap is within visible light energies. These Si-rich regions around the pores are considerably more reactive than regions that are not Si-rich. Accordingly, lower levels of light intensity can be used with these highly reactive regions to induce the desired charge to the surface of the pore.

The combination of the irradiation from the light source and the properties of the nanopore membrane material produces a measurable change in conductance of the pore not induced by a thermal effect. In accordance with some aspects, the change in conductance is an increase in conductance of at least 2%, 5%, 10%, 50%, 100, 150%, or 200% compared to the conductance without irradiation from the light source. Larger increases in conductance may also be obtained. The conductance of the pore after irradiation from the light source may be in the range from 0.1 nanosiemens to 1000 nanosiemens, more particularly from 1 to 200 nanosiemens. The irradiation from the light source also results in an increase in charge density of the surface of the nanopore. The induced charge may be positive or negative. Negative charge can be used to reduce translocation speed of anionic biopolymers. The resulting charge density may be at least 20, or at least 50 milliCoulomb/$m^2$, more particularly at least 500 milliCoulomb/$m^2$, and in some cases, at least a few Coulombs/$m^2$.

In accordance with another aspect, the present application also provides a method for unblocking clogged pores. Increasing the laser power to a few milliwatts results in the immediate release of any stuck charged biopolymer inside or around the pore. This process is explained by the intense repulsion between the charged biopolymer, which repels the biopolymer from the similarly charged pore walls, and the strongly charged pore, as well as with the high water flow. This allows for an easy, immediate and repeatable way to clear any blocked or clogged pores, which is a constant problem with nanopore technologies.

Additionally, the translocation speed can be further manipulated by coating the surface of the pore with one of multiple species of charged organic or inorganic molecules. The coatings can then be used to create a "gated-pore" which can be opened or closed at will, depending on the magnitude of the attracting or repelling forces between the coated polymer and the pore walls. This attraction or repulsion can be finely tuned by modifying the number of surface electrostatic charges. It would then be possible to open or close the pore to any desired degree by adjusting the light intensity. Thus it is foreseeable to tweeze a single molecule of DNA as it is being translocated by closing or narrowing the pore at the right time and subsequently releasing the molecule by re-opening it. Modulation of the translocation speed can be achieved in the same way, by adjusting the laser intensity to obtain the desired amount of interaction between the DNA and the surface polymer.

Various coating materials may be employed, depending on the particular application. Suitable coating materials have been described in U.S. patent application Ser. No. 12/599,440, the contents of which are hereby incorporated by reference. For example, various silanes include a first moiety which binds to the surface of a semiconductor membrane and a second moiety which binds to various tethered molecules. These silanes include, without limitation, 3-glycidoxypropyltrialkoxysilanes with C1-6 alkoxy groups, trialkoxy(oxiranylalkyl)silanes with C2-12 alkyl groups and C1-6 alkoxy groups, 2-(1,2-epoxycyclohexyl)ethyltrialkoxysilane with C1-6 alkoxy groups, 3-butenyl trialkoxysilanes with C1-6 alkoxy groups, alkenyltrialkoxysilanes with C2-12 alkenyl groups and C1-6 alkoxy groups, tris[(1-methylethenyl)oxy]3-oxiranylalkyl silanes with C2-12 alkyl groups, [5-(3,3-dimethyloxiranyl)-3-methyl-2-pentenyl]trialkoxysilane with C1-6 alkoxy groups, (2,3-oxiranediyldi-2,1-ethanediyl)bis-triethoxysilane, trialkoxy[2-(3-methyl-oxiranyl)alkyl]silane with C1-6 alkoxy groups and C2-12 alkyl groups, trimethoxy[2-[3-(17,17,17-trifluoroheptadecyl)oxiranyl]ethyl]silane, tributoxy[3-[3-(chloromethyl)oxiranyl]-2-methylpropyl]silane, any alkylsilane where the alkyl groups have a varying length between 3 and 30 carbons, and combinations thereof. Silanes can be coupled to the semiconductor membrane according to a silanization reaction scheme (see, for example, PCT Publication Nos. WO 2006/0278580 and WO 2002/068957, the contents of which are hereby incorporated by reference in their entireties).

By controlling the properties of the film used for coating the nanopores, the characteristics of the nanopore may be refined for a variety of applications. The ex situ method for chemical functionalization of nanopore surfaces includes a sequence of chemical coating steps alternated with measurements to detect coating thickness, composition and surface characteristics. Film thickness, roughness and chemical composition of the different films on planar SiN substrates may be determined through ellipsometry, non-contact atomic force microscopy (AFM) and X-ray photoelectron spectroscopy (XPS). AFM characterization on these films yielded RMS roughness values in the range 0.4-0.7 nm, similar to uncoated SiN (0.58 nm), implying a homogeneous film distribution.

Applications

The present application describes methods for using low power visible light to induce retardation of DNA translocation through solid-state nanopores by more than an order of magnitude via optically driven modulation of the nanopore surface charge density. Starting with weakly charged nanopore surfaces in darkness, focusing just a few mW of visible laser on a $SiN_x$ membrane which has been exposed to a high-power electron beam can induce surface charge densities of the order of a Coulomb per $m^2$. These highly charged nanopores can produce significant surface currents which in turn create an EOF moving in opposition to the anionic translocating molecule, resulting in a strong increase of translocation time and a slight decrease in capture rate. This effect can be controlled analogically and rapidly (within µs) by simply adjusting the laser power. Its dynamic range is determined by the local N/Si stoichiometry, which is affected by exposure to an electron beam during the pore drilling process. A first order model that accounts for the light-induced current enhancement in the nanopore fits the data well, and can be used to obtain quantitative values for pore photo-reactivity. Ultra-fast and reversible modulation of surface charges is a fundamental feature of nanosciences and nanotechnologies. It plays important roles in diverse areas ranging from bio-sensing to synthetic biology. By exploiting the intrinsically high sensitivity of the ion current flowing through nanopores to small modulations in their surface charge, the effect of low-power visible light on the nanopore surface charge can be characterized. The present application describes methods to reversibly slow down DNA translocation through nanopores, which is a critical milestone for emerging nanopore sequencing technologies. However, modulation of surface charge in confined areas is fundamentally important to any nanosensor that interacts with charged biomolecules, and nanopores are merely one device in which the effects discussed here may be characterized. The general phenomenon presented herein could be useful for a plethora of other nanosystems bearing similar material properties.

Nanopores are an emerging class of single-molecule sensors capable of probing the properties of nucleic acids and proteins with high-throughput and resolution. Nanopores are extremely sensitive single molecule sensors, which have been recently used for the detection of biopolymers such as DNA and RNA. One of the most promising applications for nanopores is ultra-fast DNA sequencing. An outstanding issue in the implementation of nanopore sequencing is the high speed at which the biopolymers translocate through the pore. In order to distinguish between the four different nucleotides in the DNA, a sufficient integration time should be realized in the readout process. Current results show that the translocation time of each single nucleotide is two to three orders of magnitude faster than the desired speed. Although efforts have been made to reduce the translocation speed, e.g., by increasing the fluid viscosity, only a small decrease of the speed was observed, coupled to attenuation of the ion current signal used for nucleotide probing. Current decreases with increases in viscosity, resulting in a decreasing signal-to-noise ratio and ion current signal degradation.

In nanopore experiments, a voltage is applied across a thin insulating membrane containing a nanoscale pore, and the ion current of an electrolyte flowing through the pore is measured. Upon introduction of charged biopolymers to the solution, the local electrical field drives individual molecules through the nanopore. Passage of biopolymers through the pore causes fluctuations in the measured ion current that directly correspond to their local cross-section. While other single-molecule techniques (e.g., atomic force microscopy) rely on a movable sensor to detect the properties of surface-immobilized biomolecules, the nanopore is spatially fixed, with the molecules being driven to the nanopore sensor. This allows a very large number of single biopolymers to be probed without chemical modification (conserving structure/function). This also eliminates the need for surface immobilization, thereby providing higher throughput. These attractive features have set the stage for the development of novel nanopore-based applications, such as detection of genetic variability, probing DNA-protein interactions, and low-cost, high-throughput DNA sequencing.

Central to all such nanopore methods is the objective of controlling the translocation process at a level that allows spatial information to be resolved at the nanometer scale, within the finite time resolution imposed by instrument bandwidth and noise. To achieve this goal, developing a fundamental understanding of the factors governing the DNA translocation dynamics, and its relationship with the magnitude and fluctuations in the blocked current signal, is desirable. To date, most DNA translocation studies have been performed using the toxin α-hemolysin (α-HL), which can only admit single-stranded DNA (ssDNA) and RNA (but not double-stranded nucleic acids). Typical translocation velocities for ssDNA through the α-HL channel are $v_T \sim 0.2$ mm/s (measured at 120 mV and RT), corresponding to translocation times of $\tau_T(N)=l/Nv_T \approx 2$ µs/base (N=number of nucleotides, 1 is the DNA contour length), approaching feasible temporal resolution for single-base detection. However, biotechnological nanopore applications require size tunability and membrane robustness, not available with phospholipid-embedded protein channels.

Recent progress in the fabrication of nanoscale materials has enabled the reproducible formation of artificial, well-defined nanopores in thin, solid-state membranes. Most DNA translocation studies have focused on relatively large pores (8-20 nm), for which the translocation dynamics were markedly faster ($v_T \sim 10$ mm/s or 30 ns/bp). In addition to the fast dynamics, the use of large nanopores necessitated performing measurements at smaller temporal bandwidths than with α-HL experiments (10 kHz vs. 100 kHz, respectively). This results in degradation of the ion current signal, which compromises the spatial resolution of the analyzed biopolymer. Slowing down biopolymer translocation is therefore a key goal for improving the analytical capabilities of nanopores.

In accordance with another aspect, nanopores can be used to study protein molecules. Protein molecules are nature's laborers, carrying out a variety of precise tasks, such as molecular recognition, chemical catalysis, and molecular transport. By articulating the solid-state nanopores with individual protein molecules, these functions can be probed with unprecedented efficiency and sensitivity. Molecular recognition can be studied by immobilizing a single protein molecule in the nanopore, and then observing ion current blockades during binding of analytes. Enzyme catalysis can be studied at the single-molecule level by optical probing of fluorogenic products of the catalysis reaction by enzymes immobilized inside nanopores, while using ion-current measurements for additional control over activity and analyte concentration. Molecular transport through protein channels can be engineered by immobilizing a single protein channel inside a nanopore. Since the immobilized protein molecule is immobilized at the junction connecting the two membrane sides, it can be subjected to chemical gradients, or conversely it can pump molecules from side to side to create chemical differences.

Examples

A high-resolution transmission electron microscope (TEM) was used to fabricate a single nanopore in silicon nitride membranes 30 nm thick. Piranha-cleaned chips were freshly assembled in a custom-made Teflon cell permitting low-noise electrical measurements and direct imaging using a high-magnification microscope objective (see Methods and FIG. 1a). A tightly-focused green laser (532 nm) in a custom-made confocal microscope illuminated the nanochip while a nanopositioner scanned a 4×4 μm² area of the silicon nitride membrane. The ionic current (I) flowing through the pore at a fixed voltage level was continuously recorded during scanning.

Figure 1:
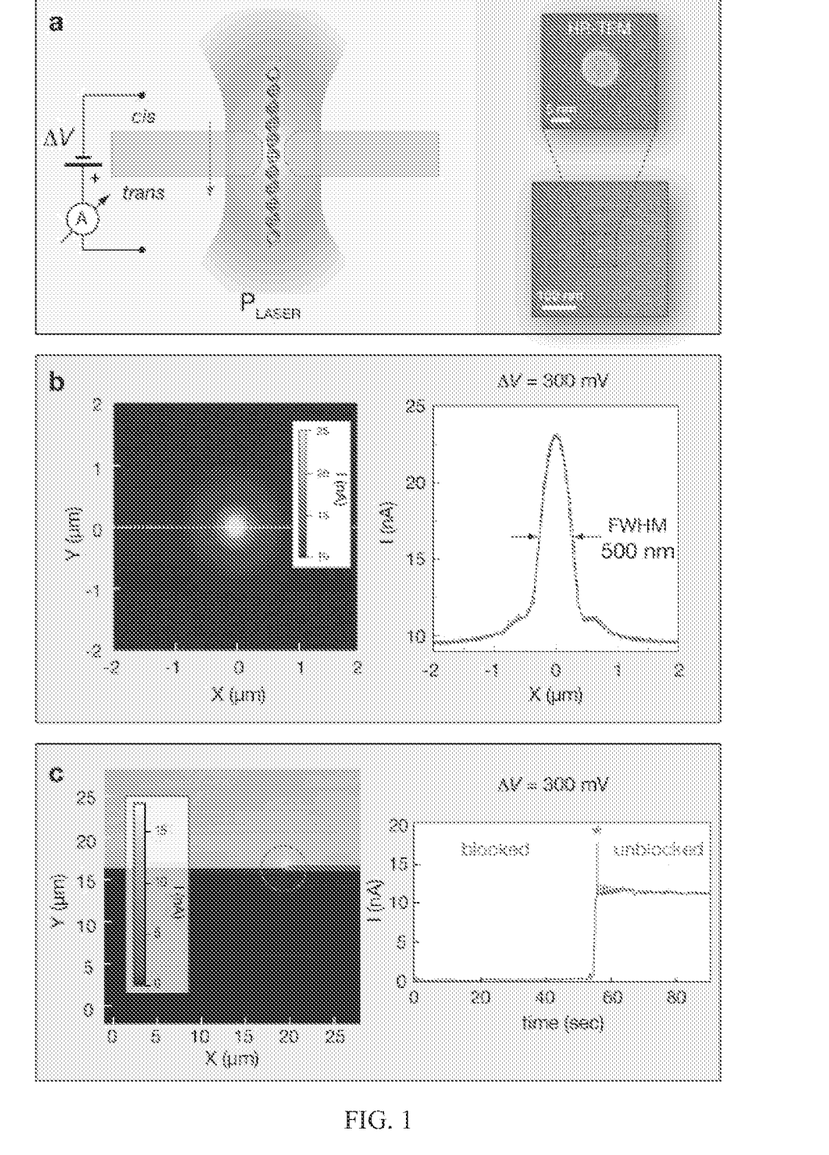
FIG. 1A illustrates a schematic picture of the confocal optical nanopore setup. A solid state nanopore is positioned at a laser beam focus by a nano-positioner, and the ion-current flowing through the pore is measured before and during translocation of DNA molecules. The inset shows high-resolution Transmission Electron Micrographs of a typical pore (10 nm).
FIG. 1B Left: provides a surface plot showing nanopore ionic current enhancement as a 10 mW focused laser beam ($\lambda$=532 nm) scans the 4×4 $\mu m^2$ SiN membrane at 1 $\mu m/s$. When the focused beam reaches the nanopore it produces a significant increase in measured current (2.4-fold increase for this pore). Right: shows a line profile through Y=0, fitted using a Gaussian function with FWHM of ~500 nm, consistent with the diffraction limit.
FIG. 1C illustrates clearing a blocked solid-state nanopore with light. Left: a 5 mW laser intensity raster scan of the entire SiN window (30×30 $\mu m^2$, lower left to top right). The map represents the current flowing through the pore at $\Delta V$=300 mV. As soon as the laser beam overlaps with the nanopore location, it clears the pore and thereafter the ionic current stabilizes at the open pore level of 12 nA. Right: time trace of I during the laser scan.

Surprisingly, when the laser spot overlapped with the nanopore location there was an increase in I, with maximum magnitude more than twice that of the original current. This effect was evident even when using laser powers of just a few mW. This photo-conductance effect is illustrated in FIG. 1b: The upper panel shows TEM images of the 10 nm pore used in this test at two magnifications for reference. The middle panel shows an intensity surface plot of the ionic current I flowing through this pore as a function of laser spot position. A line scan through the center of the image reveals a clear symmetric peak in the ionic current with a FWHM of ~500 nm (right panel). This effect was observed in all tested pores, using diameters ranging from 4 to 20 nm. Although it has been shown that an IR laser (1064 nm) at high power (~1 W) can produce a small increase in current by locally heating the solution, in the present case laser-induced heating can be ruled out as the origin of the conductance increase for two reasons: the electromagnetic absorption of water at 532 nm is extremely small, and the laser powers used in this experiment are only of a few mW. Specifically, the observed two-fold increase in the ionic current would correspond to a temperature jump of 35° K. Additionally, based on four (4) measurements performed at 800 nm (where water absorption is larger), it can be estimated that heating accounts for a mere 5 mK per mW of focused light.

Permanent nanopore blocking by small molecules, tiny air bubbles, or other nanoscale particulates is a common limitation for nanopore sensors, severely reducing their functional lifetime. In some cases, a series of electrical pulses clears the pore, but often the system must be disassembled and re-cleaned. As disclosed herein, in many of these cases a short exposure to a ~5 mW focused laser beam will immediately clear the nanopore. FIG. 1c (left) shows a raster scan (bottom left to top right) of a fully blocked nanopore (I≈0 at V=+300 or −300 mV). As soon as the laser beam reaches the nanopore location, the pore is cleared. Thereafter, I stabilizes at the open pore level of 12 nA. This is shown chronologically (FIG. 1c, right) as a time trace of I during the laser scan. Light-induced nanopore unblocking is a highly robust and efficient tool to extend the functional lifetime of solid-state nanopores from a few hours to several days.

The effect of the photo-conductance phenomenon on the translocation dynamics of DNA through solid-state nanopores was then investigated. Over 1,000 translocation events of 10 kbp DNA were acquired in a nanopore (5.4 nm) in the dark (laser power P=0). At t=150 s the laser radiation was switched on (P=2 mW, pre-aligned with nanopore) as the software continued to record translocation events. Representative events before, during, and after illumination are shown in FIG. 2a. Three features are immediately apparent: (i) the open pore current ($I_O$) and the current during translocation ($I_B$) both increased when the laser was turned on, (ii) the average event amplitude $\Delta I = I_O - I_B$ remained at the same level of 0.78±0.10 nA under both conditions, and (iii) the mean event dwell-time $t_D$ increased by roughly a factor of 10 under illumination, as compared to dark conditions. These features are illustrated in FIG. 2b, which shows $I_O$ and $\Delta I$ as a function of time throughout the experiment (top panel). A 150-event running window average over all translocations (bottom panel) indeed shows a tenfold increase in the translocation time from ~1 ms to ~10 ms under laser illumination. As used herein, the term "Retardation Factor" (RF; here RF=10) is defined as the increase in mean translocation time under laser light relative to darkness. Upon switching off the laser illumination at t=300 s, $I_O$ returned to base level (3.6 nA) and the mean translocation dwell time was restored to ~1 ms, suggesting that this effect is completely reversible. This experiment was repeated for nanopores of various sizes, and in all cases a marked retardation of translocation time under laser illumination was observed.

The above measurements were repeated using a range of DNA lengths in several different nanopores and under different laser powers. The results are summarized in FIG. 2c, where the measured RF is plotted against laser power for five different nanopores with diameters of 4.3, 5.4, 5.6, 6.1, and 7.4 nm (diamonds, squares, upward triangles, circles and downward triangles, respectively). In each of these experiments, the mean translocation time was measured by obtaining at least 1,000 events per laser intensity, and fitting the histograms with exponential functions as previously described. Four different DNA lengths were used in these experiments, 400 bp, 3.5 kbp, 5 kbp, and 10 kbp. These and other measurements suggest that the amount of retardation per mW of light does not seem to correlate with either pore size or DNA length. Instead, as will be shown later, it depends strongly on the properties of the surrounding material.

Figure 3:
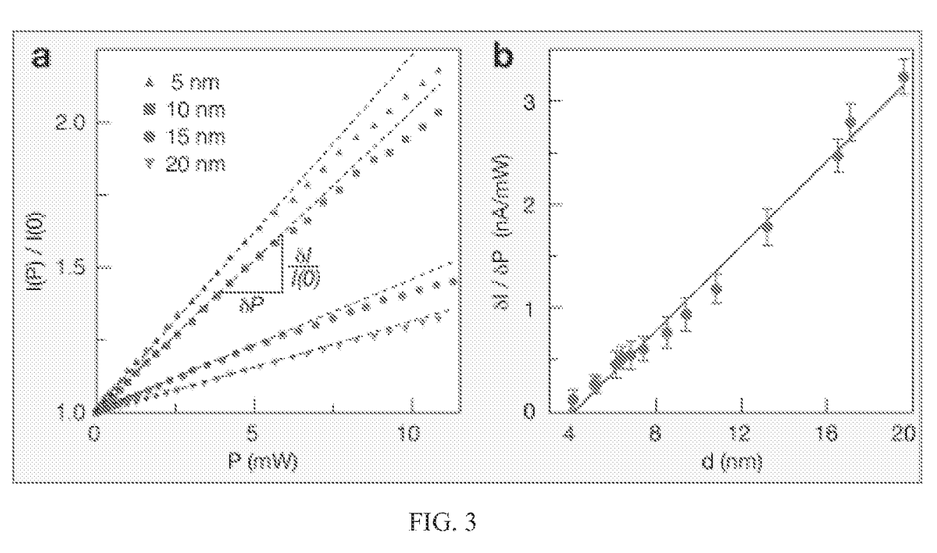
FIG. 3 shows ionic current enhancement as a function of laser power and pore diameter.

To elucidate the physical origin of light-induced retardation of translocation, the pore current I was characterized at varying laser intensity P for a range of nanopore sizes (4-20 nm diameter, d). FIG. 3a displays ionic current enhancement (I(P)/I(0)), for four representative pores (d=5, 10, 15, 20 nm). In each of these cases, I is linear for P<5 mW, above which I deviates slightly from linearity. Linear fits for P<5 mW characterize the response of each pore to light as the initial slope δI/δP. A plot of δI/δP as a function of diameter for 14 pores (4-20 nm) exhibits a clear linear dependence on d (FIG. 3b). This suggests that when the $SiN_x$ thickness L and nanopore drilling conditions are maintained, the pores response to light per their surface area (πdL) is a constant. From FIG. 3b, a value of $2.2 \times 10^{-3}$ nA mW$^{-1}$ nm$^{-2}$ can be calculated.

Figure 2:
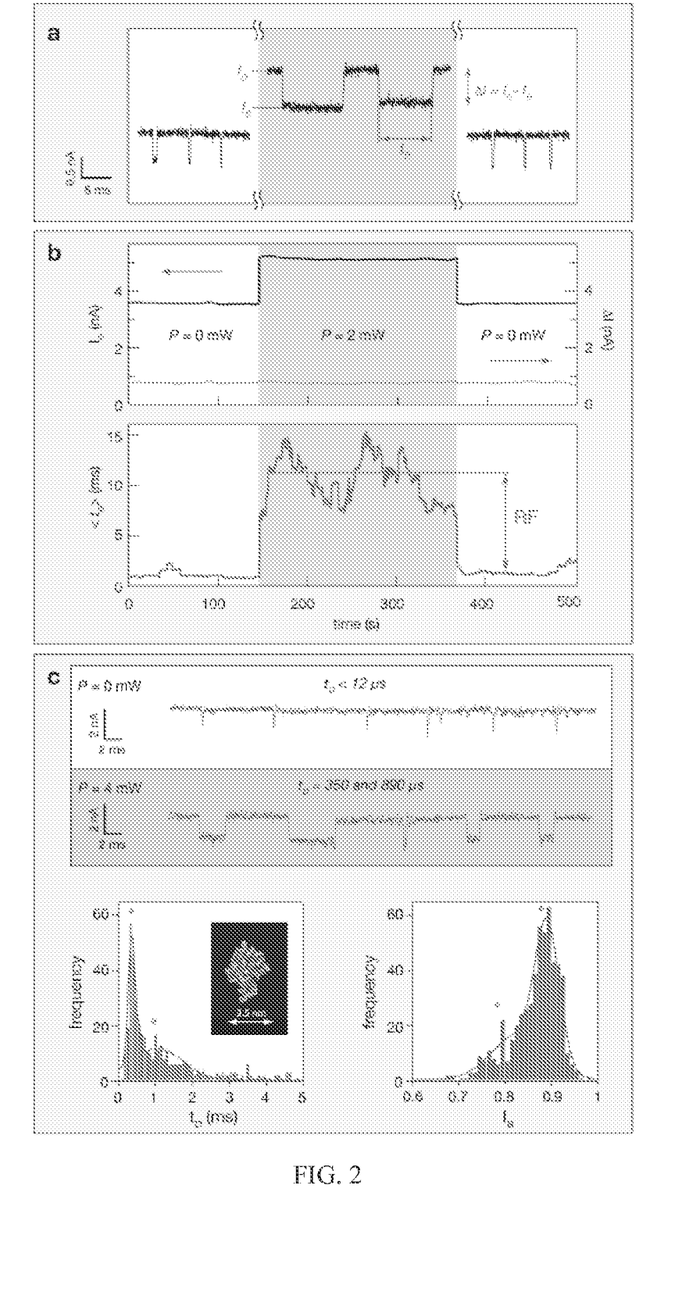
FIG. 2 illustrates slowing down DNA and protein translocation speed with light.

The linear dependence of δI/δP on nanopore diameter suggests that photo-conductance current enhancement is a surface phenomenon rather than a volumetric one (which would exhibit ∝d² dependence). Solid-state nanopores possess weak surface charge, which can dominate pore conductivity at salt concentrations lower than ~100 mM. However, it has been theorized that high charge densities on nanopore walls can affect electrical conductivity even under high salt conditions. Surface charges induce a diffuse double layer containing an excess of oppositely charged ions, of thickness comparable to the Debye screening length $\kappa^{-1}$. Ionic current is enhanced by the electrical double layer in two ways: (i) by creating a local imbalance of counter ions within $\kappa^{-1}$, which (ii) drags water molecules with its motion, creating an electro-osmotic flow (EOF) which in turn pulls along additional current (see FIG. 4a). The total ionic current for a nanopore with a charged surface is:

$$I = I_{bulk} + I_{DL} + I_{EOF} \qquad (1)$$

where $I_{bulk}$ is the current due to ions outside the electrical double layer, $I_{DL}$ is the current due to ions forming the double layer, and $I_{EOF}$ is the current due to net water flow induced by net movement of ions within the double layer. $I_{EOF}$ is proportional to the product of the flow velocity field and the net charge density ρ(r), which is only nonzero within $\kappa^{-1}$. For small $\kappa^{-1}$ compared to the pore diameter, (e.g., $\kappa^{-1} \approx 0.3$ nm at 1M KCl at 21° C.), only $I_{bulk}$ scales with cross sectional area ($I_{bulk} \propto \pi d^2$) whereas $I_{DL}$ and $I_{EOF}$ scale with circumference ($I_{DL}, I_{EOF} \propto \pi d \kappa^{-1}$)($I_{DL} \times I_{EOF} \propto 2\pi R \kappa^{-1}$). Thus, surface charges can, in principle, explain increased I as well as its linear scaling with d. Moreover, if the analyte remains mostly within the bulk pore volume where there is no charge imbalance, $\kappa^{-1}$ distance away from the pore walls, it is expected that $\Delta I$ will be independent of surface charge—and thus independent of P. This is consistent with what is observed (FIG. 2).

Surface charge on a nanopore will affect (i) translocation times and (ii) polymer capture rate. A negatively charged nanopore produces an EOF towards the cathode (cis chamber, FIG. 4a), increasing drag on a negatively charged translocating polymer, resulting in longer translocation times and reduced polymer capture rates. Conversely, positive surface charges would enhance capture rate and reduce translocation times. The results shown in FIG. 2 indicate that the RF for DNA translocation grows with laser intensity. Moreover, DNA capture rate was reduced by 30%, from 11 s$^{-1}$ to 8 s$^{-1}$, for 2 mW of laser light. These observations lead us to hypothesize that visible light can induce negative surface charges on silicon nitride, which in turn slows DNA translocation through the drag created by EOF moving in the opposite direction of DNA.

To validate this hypothesis it was approximated that for low laser powers the surface charge density ($\sigma$) grows linearly with laser intensity, such that $\sigma = \gamma P$ where $\gamma$ is the photo-reactivity of the pore (C. m$^{-2}$ W$^{-1}$). The total ionic current I can be obtained as a function of surface charge density using the following three individual contributions: (i) $I_{bulk}$ is the electrophoretic movement of each ion species through the nanopore; (ii) $I_{DL}$ may be determined from the net charge distribution $\rho$ for a given wall potential, derived analytically from the Poisson-Boltzmann equation and from the Boltzmann distribution, assuming a cylindrical nanopore and using the Debye-Hückel approximation; (iii) $I_{EOF}$ is a product of $\rho$ and the EOF velocity profile described by the Navier-Stokes equation. The Grahame equation may be substituted to give $\sigma$ as a function of wall potential. The contributions to the ion current are:

$$I_{bulk} \approx e n_{KCl}(\mu_K + \mu_{Cl}) \frac{\pi d^2}{4L} \Delta V \quad (2.1)$$

$$I_{DL} \approx \frac{2\pi d \varepsilon \kappa \mu_K}{L} \sinh\left(\frac{\beta e \gamma P}{2\kappa \varepsilon}\right) \Delta V \quad (2.2)$$

$$I_{EOF} \approx \frac{2\pi d \kappa \varepsilon^2}{L \eta \beta^2 e^2} \left[\sinh^{-1}\left(\frac{\beta e \gamma P}{2\kappa \varepsilon}\right)\right]^2 \Delta V \quad (2.3)$$

for elementary charge e, permittivity of aqueous solution $\varepsilon$, parameter $\beta = 1/k_B T$ (Boltzmann constant $k_B$, absolute temperature T), pore length L, applied voltage clamp $\Delta V$, and solution viscosity $\eta$. The number density of potassium or chloride ions is $n_{KCl}$, with electrophoretic mobilities $\mu_K$ and $\mu_{Cl}$. Nanopore diameter d can be determined from TEM images, enabling a quantitative estimation of the nanopore photo-reactivity $\gamma$ via Eq.2. The dependence of I on KCl concentration (0.01 M to 1 M) was also measured at different P and found to be consistent with the model.

Additional DNA translocations were performed using a range of DNA lengths, nanopores, and laser powers to determine the role of surface charge in slowing translocation speed. The results are summarized in FIG. 4b (left), where RF is plotted against P for five nanopores (4.3, 5.4, 5.6, 6.1, and 7.4 nm diameters) and four DNA lengths (0.4, 3.5, 5, and 10 kbp). $t_D$ was measured for >1,000 events per laser intensity, and the $t_D$ histograms were fitted with exponential functions as previously described. These measurements suggest that RF per mW of light widely varies with pore size and DNA length.

Figure 4:
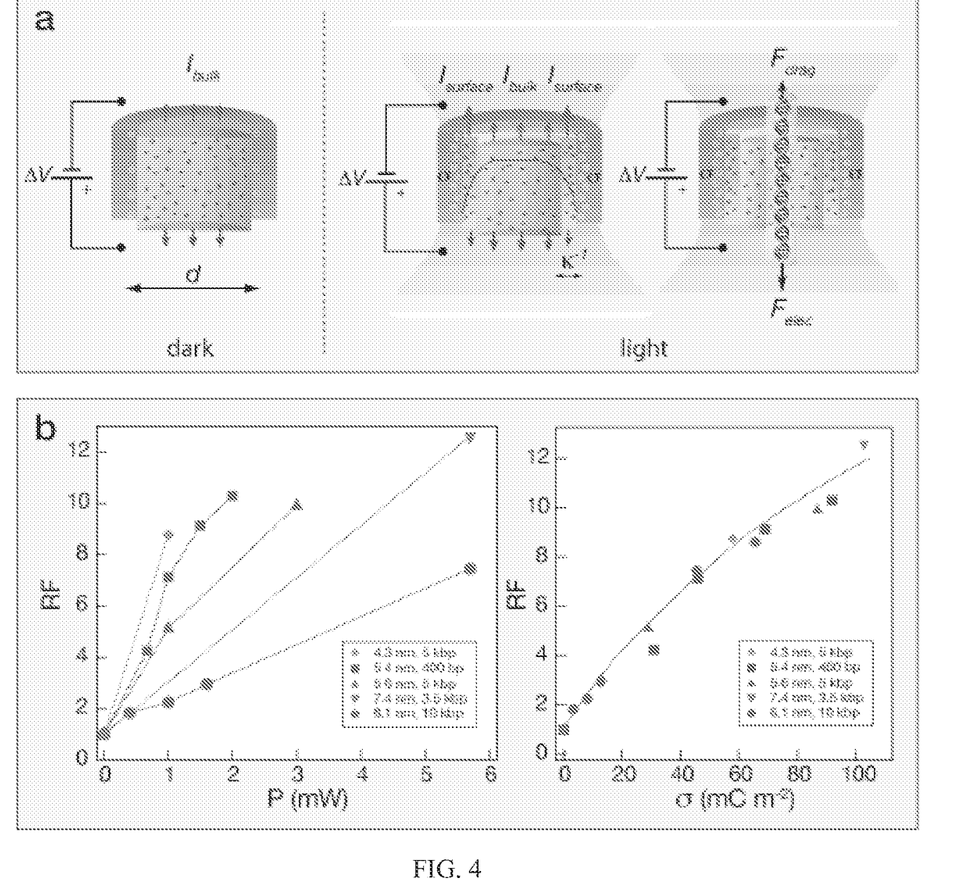
FIG. 4 illustrates that light-induced surface charge density modulates the EOF and DNA translocation speed.

Fitting Eq. 2 as described above to obtain $\gamma$ for each of the pores, the DNA RF is transformed into surface charge density $\sigma$ using the relationship $\sigma = \gamma P$. Remarkably, all data points collapse onto a single curve (FIG. 4b, right). Thus, light-induced slowing is dependent only on the induced surface charge density $\sigma$. Controlling the RF value can be achieved either by selecting a highly optically reactive pore (high $\gamma$) under low laser intensity, or using a less optically reactive pore under higher laser intensity.

Drilling nanopores in SiN$_x$ with an electron beam reduces the N/Si ratio around the pore due to preferential ablation of N atoms. Moreover, the principal defects in silicon-rich CVD amorphous SiN$_x$ materials are Si dangling bonds, which can trap electrons or holes to become charged. When the N/Si ratio approaches 0.8, the band gap is within visible light energies. When the N/Si ratio of the material surrounding the pore is low enough, it is proposed that visible light can excite electrons from the ground state across the band gap, trapping them in Si dangling bonds. Eventually, trapped electrons would recombine with holes, but a high density of arriving photons could maintain a steady state of negatively charged Si dangling bonds, creating a net surface charge density.

Figure 6:
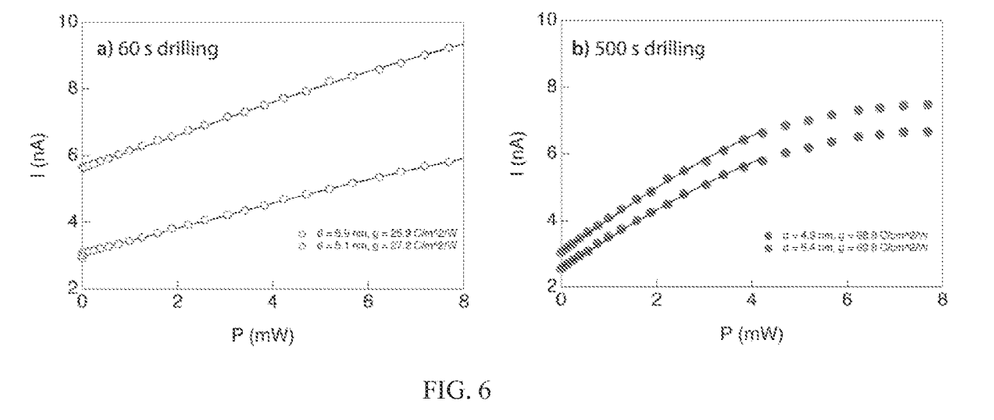
FIG. 6 provides graphs showing the results of measurements of the photo-reactivity of four similar nanopores drilled by exposing the SiN membrane to the e-beam for either 60 s (left, empty symbols) or 500 s (right, solid symbols).

To check this theory, four additional nanopores were TEM-drilled, all with similar diameters, in a freshly deposited SiN$_x$ membrane. Since longer e-beam exposure produces pores with lower N/Si ratios, two nanopores were drilled by exposing the membrane for 60 s, and two were drilled with 500 s of exposure to produce different local N/Si stoichiometry. These pores were assembled in the confocal microscope and their optical reactivities were measured. FIG. 6 shows the measured current versus laser power and the corresponding fits. Strikingly, the pores drilled with a low e-beam dose had relatively low photo-reactivity ($\gamma = 27$ C. m$^{-2}$ W$^{-1}$), whereas the pores exposed to a high e-beam dose had much higher photo-reactivity ($\gamma = 70$ C. m$^{-2}$ W$^{-1}$). This establishes a direct correlation between e-beam dosage and the optical reactivity of a nanopore.

The photo-conductive effect was tested for analytes other than DNA. Previous studies have sensed proteins such as bovine β-lactoglobulin or avidin in solid-state nanopores, and antibodies such as anti-biotin Fab fragments or anti-biotin in lipid coated nanopores. However, the detection of small proteins (MW<10 kDa) in their native state remains a major challenge, since these proteins translocate through the pore too quickly to produce a resolvable signal given current bandwidth limitations.

Ubiquitin (MW~8.5 kDa, 4 nm diameter), relevant to a broad range of biological processes, was selected as a representative small protein to demonstrate that the photo-conductive effect can slow small protein translocations and enable their detection and characterization. Under dark conditions, purified wild-type ubiquitin translocating through a ~5 nm pore yielded sporadic, brief downward spikes (top trace, FIG. 2c). The dwell time of these spikes was estimated to be <12 μs, but neither this nor the current amplitude of ubiquitin translocations could be accurately determined due to bandwidth constraints even at 100 kHz, suggesting that the true translocation dwell time of these proteins is shorter than estimated.

Laser illumination of the same nanopore at P=4 mW resulted in a marked increase in both the frequency and average dwell time of detected ubiquitin events (bottom trace, FIG. 2c). The average translocation time increased by at least two orders of magnitude, allowing full characterization of both amplitude and dwell times for ubiquitin translocations. The increase in event rate under illumination may be attributed to events that were previously undetectable under dark conditions due to bandwidth limitations. As with DNA translocations, this effect was completely reversible.

A typical dwell time distribution and fractional blockade current ($I_B$) for illuminated ubiquitin translocations are shown in FIG. 2c (N>500). Two prominent timescales are observed for ubiquitin translocation (340±5 and 890±70 µs), as well as two peaks in the blockade currents (0.88 and 0.78), approximated by a sum of two Gaussians. Although not wishing to be bound by theory, it is hypothesized that the two peaks observed in these distributions may be associated with different orientations of the asymmetric "mushroom-like" ubiquitin (inset) during translocation. This hypothesis is consistent with previous reports for other protein/DNA complexes.

Figure 5:
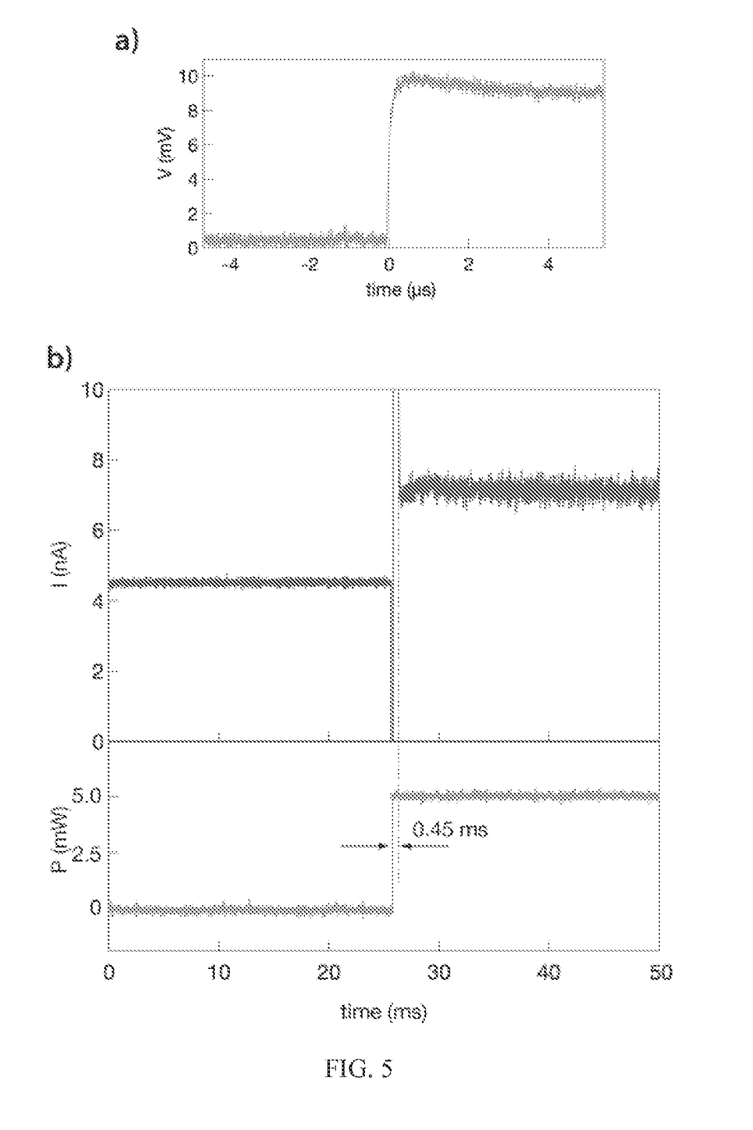
FIG. 5 illustrates the measurement of the temporal response of the optoelectrical effect in a solid-state nanopore.

To characterize the temporal response of the photoconductive effect a "laser on/off" TTL pulse from a DAQ card was connected to the Analog modulation control of the iFlex 2000 solid-state laser (QIOptiq). According to the laser specifications the rise time of the system is <200 ns. This was confirmed by measuring the actual rise time with a fast photodiode (PDA36A, Thorlabs) connected to a digital 100 MHz scope (TDS3014C, Tektronix). A LabView program was written to switch the laser on/off while measuring the ion current through a solid-state nanopore positioned at the laser focus, as explained in the main text. The laser intensity rise time measured by the photodiode shows characteristic switching time of <0.2 µs (FIG. 5a). The simultaneous measurement of the ionic current flowing through a 5 nm pore (V=300 mV, C=1 M KCl) and the laser intensity are shown in FIG. 5b. An abrupt jump of the current from 4.4 nA to 7.1 nA was observed, concurrent with the laser switching on time. The delay time from switching on the laser light to the stabilization at the current at the higher level was measured to be 0.45 ms, and is attributed to the transient saturation of the Axon amplifier upon an abrupt increase in pore conductance.

The present application shows that just a few mW of visible laser light focused on a nanopore can induce surface charge densities up to ~1 C. m$^{-2}$, much larger than the weak native charge of $SiN_x$. Increased σ produces net charge near the pore walls, which, under external voltage, creates an electro-osmotic flow moving in opposition to an anionic translocating molecule. This flow slows translocating DNA and proteins, allowing detection and characterization of small analytes, such as ubiquitin. Previous approaches to slowing analyte translocation have introduced permanent modifications to the nanopore walls, inducing stronger interactions of analytes with the pore surface during translocation. By contrast, the optoelectronic effect allows completely reversible, in-situ control of σ and translocation speed without permanently altering the surface properties of the nanopore or buffer. This is particularly useful for detection and characterization of molecules in their native form. Moreover, ultra-fast tuning of surface charge by light completely decouples the capture process from subsequent translocation. Solid-state lasers, as well as other light sources, can be readily switched on/off in sub-µs timescales, and hence induce current jumps in the nanopores within milliseconds. The dynamic range of the photoconductive effect is determined by local N/Si stoichiometry, which in turn depends on e-beam exposure during nanopore drilling. The method described herein will facilitate a broad range of emerging nanopore sensing applications, including genotyping using Peptide Nucleic Acid (PNA) probes and quantification of epigenetic markers.

Ultra-fast and reversible modulation of surface charge is fundamentally important for the development of novel nanosensors. By exploiting the intrinsically high sensitivity of the nanopore ionic current to small modulations of surface charge, the present application characterizes a new optoelectronic effect, models the increase in electric conductance under visible laser illumination, and proposes an underlying mechanism. Three useful applications of the technique include, but are not limited to: (i) clearing blocked nanopores and thus significantly extending their useful lifetime; (ii) slowing and tuning the translocation speed of DNA; and (iii) detecting and characterizing translocation events of very small proteins, such as ubiquitin. Together, these milestones broaden the range of molecules that can be probed by solid-state nanopores, enhance nanopore sensitivity, and extend the lifetime and throughput of individual pores.

Methods

Nanopores were drilled on low-stress (silicon-rich), amorphous LPCV-deposited $SiN_x$ membranes 30 nm thick. Chips were then cleaned using Piranha solution and kept in water until mounted on the Teflon holder, rendering two independent chambers connected by the nanopore and filled with an electrolytic solution (1M KCl, 20 mM TRIS, pH 8.0, 21° C.). A pair of Ag/AgCl electrodes was used to apply an electrostatic potential difference across the chambers separated by the insulating $SiN_x$ membrane. The resulting ionic current through the nanopore was recorded using a patch-clamp amplifier (Axopatch 200B, Molecular Devices Cooperation). The whole apparatus was shielded from external electromagnetic noise by a Faraday cage. The electrical readout from the amplifier was filtered with a 10 kHz low-pass Bessel filter and digitized using a 16 bit A/D card (National Instruments) controlled by a custom-written LabView (National Instruments) program.

The nano-chip was secured to a closed loop nano-positioner (Physik Instrumente) with sub-nm accuracy, also controlled by the LabView program. The nanopositioner was mounted in a custom built confocal setup, in order to simultaneously illuminate the nanopore with a focused laser beam and count individual emitted photons using two APDs (Perkin-Elmer), which were used to quantify photoluminescence emanating from the membrane. A 532 nm line from a laser diode (New Focus) was cleaned by a Glan-Thompson polarizer (Thorlabs), with the final power adjusted on demand by a half-wave plate mounted on a motorized rotating holder. This resulted in a final dynamic range of 2 µW to 17 mW with 500 intermediate values. The laser beam was expanded to completely fill the back aperture of a 60×, 1.2 NA water immersion objective (Olympus UPlanApo). The emission side contained a long-pass filter (Chroma HQ560LP) to remove any elastically scattered light, followed by a motorized mirror that acted as a shutter for the APDs and allowed direct visualization of the membrane using a CCD camera (Thorlabs DC111).

Other Embodiments

In view of the wide variety of embodiments to which the principles of the present invention can be applied, it should be understood that the illustrated embodiments are exemplary only, and should not be taken as limiting the scope of the present invention.

Other aspects, modifications, and embodiments are within the scope of the following claims. The invention may be embodied in other specific forms without departing from the essential characteristics thereof. The present embodiments are therefore considered to be illustrative and not restrictive.

INCORPORATION BY REFERENCE

The entire contents of each of the citations referenced above in the application are herein incorporated by reference.

The invention claimed is:

1. A method for characterizing an analyte comprising:
   providing a solid-state membrane comprising a nanopore submerged in a saline solution;
   optoelectronically modifying a surface of the nanopore, while the solid-state membrane is submerged in the saline solution, to cause a measurable change in the nanopore ionic conductance not induced by a thermal effect;
   applying an electric field across the solid-state membrane to generate an ion current through the nanopore and to translocate the analyte through the nanopore; and
   detecting variations in the ion current and/or light emission from the analyte, wherein the variations in current and/or in the light emission correspond to interactions between the analyte and nanopore surface.

2. The method of claim 1, wherein the change in nanopore ionic conductance due to the optoelectronical surface modification is an increase in conductance of at least 2%.

3. The method of claim 1, wherein optoelectronically modifying the surface of the nanopore comprises illuminating the surface of the nanopore with radiant energy from a light source to induce an increase in conductance of the nanopore.

4. The method of claim 1, wherein the analyte comprises a biopolymer.

5. The method of claim 4, wherein the biopolymer comprises one of single-stranded DNA, double-stranded DNA, RNA, and a polypeptide.

6. The method of claim 3, wherein the light source is a laser having a wavelength in the range from about 200-750 nm.

7. The method of claim 1, wherein the solid state membrane comprises a semiconductor or insulating material that has energy levels accessible with visible light.

8. The method of claim 3, further comprising chemically modifying the surface of the nanopore.

9. The method of claim 8, wherein chemically modifying the surface of the nanopore comprises providing a chemical coating to create a gated pore that can be widened and narrowed by adjusting the radiant energy from the light source.

10. The method of claim 1, wherein detecting variations in current comprises detecting variations in local ion current with electrodes disposed adjacent to the nanopore.

11. The method of claim 10, wherein detecting variations in local ion current comprises detecting an open nanopore current and a blocked nanopore current, the blocked nanopore current varying with respect to interaction characteristics between the analyte and the nanopore.

12. The method of claim 11, wherein the analyte comprises a DNA and the blocked nanopore current varies with respect to DNA length.

* * * * *